US011033219B2

(12) United States Patent
Bhandari et al.

(10) Patent No.: US 11,033,219 B2
(45) Date of Patent: Jun. 15, 2021

(54) APPARATUS AND METHOD FOR IDENTIFYING GAZE STABILITY OF PATIENT

(71) Applicant: Rajneesh Bhandari, Jaipur (IN)

(72) Inventors: Rajneesh Bhandari, Jaipur (IN); Anita Bhandari, Jaipur (IN)

( * ) Notice: Subject to any disclaimer, the term of this patent is extended or adjusted under 35 U.S.C. 154(b) by 249 days.

(21) Appl. No.: 15/779,095

(22) PCT Filed: Jan. 19, 2016

(86) PCT No.: PCT/IB2016/050237
§ 371 (c)(1),
(2) Date: May 25, 2018

(87) PCT Pub. No.: WO2017/089903
PCT Pub. Date: Jun. 1, 2017

(65) Prior Publication Data
US 2019/0015034 A1  Jan. 17, 2019

(30) Foreign Application Priority Data

Nov. 27, 2015 (IN) .......................... 3877/DEL/2015

(51) Int. Cl.
*A61B 3/028* (2006.01)
*A61B 3/032* (2006.01)
(Continued)

(52) U.S. Cl.
CPC ............ *A61B 5/4023* (2013.01); *A61B 3/028* (2013.01); *A61B 3/032* (2013.01); *A61B 5/11* (2013.01);
(Continued)

(58) Field of Classification Search
CPC ........... A61B 3/113; A61B 3/028; A61B 5/11; A61B 3/032; A61B 5/4023; A61B 3/0083; A61B 3/0091; A61B 5/4863; A61B 5/702; A61B 2562/0219; A61B 3/0025; A61B 5/0059; A61B 5/6803; A61B 5/7405; A61B 5/742; A61B 5/749; G06F 3/012; G06F 3/013; G06F 3/011; G06F 21/31; G06F 21/316; G06F 21/32; G06F 21/552; G06F 21/554; G06F 2221/2133; G06F 3/0346; G06F 3/041; G06F 3/0488; G06F 1/163; G06F 3/016; G06F 1/184; G06F 1/185; G02B 27/017; G02B 2027/0187; G02B 27/0093; G02B 2027/0178;
(Continued)

(56) References Cited

U.S. PATENT DOCUMENTS 7,195,355 B2 * 3/2007 Nashner ................. A61B 3/113
351/209

* cited by examiner

*Primary Examiner* — Brandi N Thomas
(74) *Attorney, Agent, or Firm* — United IP Counselors, LLC

(57) ABSTRACT

Disclosed is an apparatus and method for identifying the gaze stability of a patient. The apparatus includes a head mounted device configured to a patient head, wherein the head mounted device is adapted to track the movement of the patient head. Further, the apparatus includes a display adapted to display a graphic pattern, a perception module adapted to receive perception information regarding the patient's call out of the graphic and a data processing device adapted to control and execute the function of the display, the head mounted device, the perception module based on the inputs received from the perception module.

26 Claims, 8 Drawing Sheets

Left to right rotation

(51) Int. Cl.
  *A61B 5/00*   (2006.01)
  *A61B 5/11*   (2006.01)
  *A61B 3/00*   (2006.01)
  *A61B 3/113*   (2006.01)
  *G02B 27/00*   (2006.01)

(52) U.S. Cl.
  CPC ............. *A61B 3/0025* (2013.01); *A61B 3/113* (2013.01); *A61B 5/0059* (2013.01); *A61B 5/6803* (2013.01); *A61B 5/742* (2013.01); *A61B 5/7405* (2013.01); *A61B 5/749* (2013.01); *A61B 2562/0219* (2013.01); *G02B 27/0093* (2013.01)

(58) Field of Classification Search
  CPC ...... G02B 2027/0138; G02B 2027/014; G02B 2027/0147; G02B 27/0172
  USPC ........ 351/200, 205–206, 209–211, 221–223, 351/243–246
  See application file for complete search history.

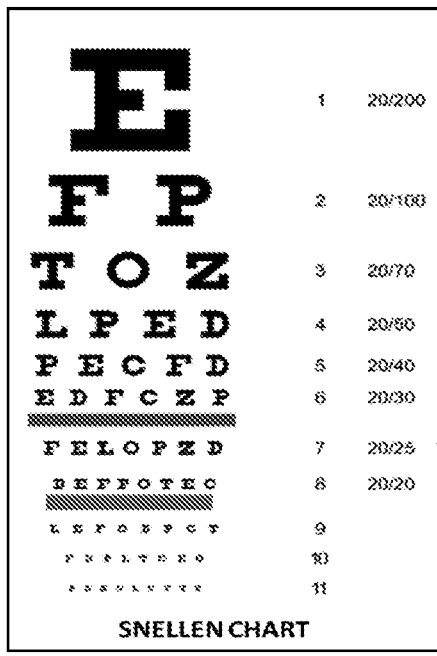
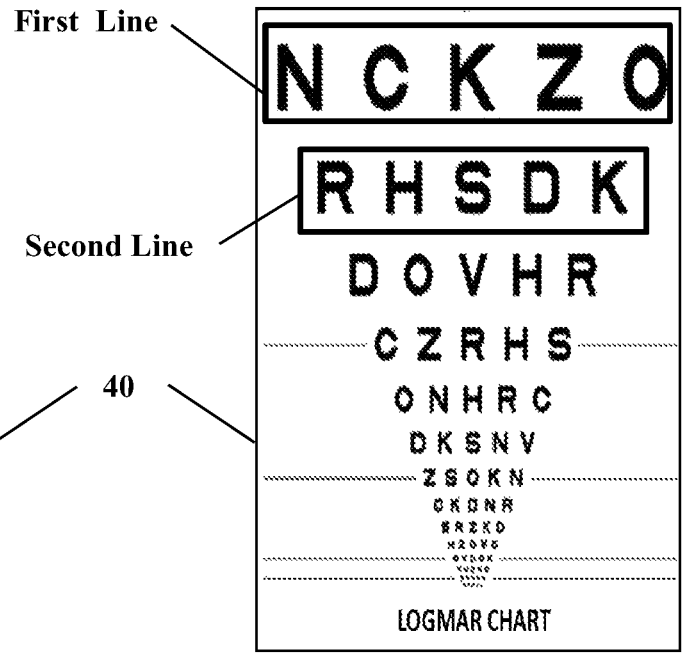
Figure 2A
Figure 2B
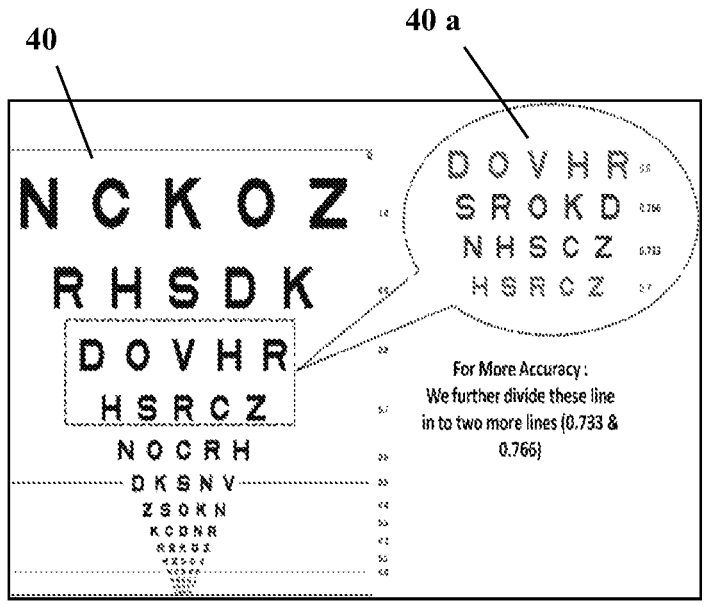
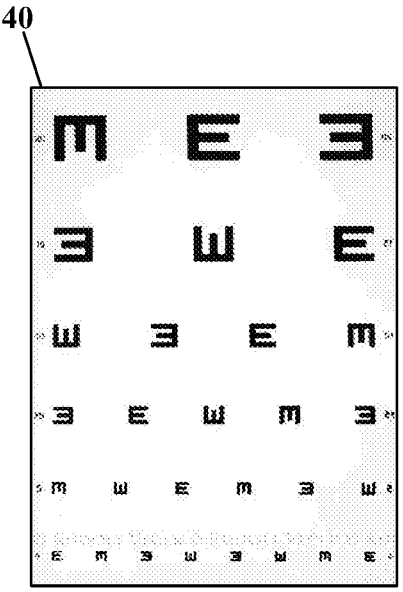
Figure 2C
Figure 2D

Left to right rotation

APPARATUS AND METHOD FOR IDENTIFYING GAZE STABILITY OF PATIENT

FIELD OF THE DISCLOSURE

The present disclosure generally relates to identification and diagnosis of vestibular disorders, such as those that may produce vertigo, dizziness, imbalance or spatial disorientation. More particularly, the present disclosure provides method and system for determining the gaze stability of the patient during head movement of the patient.

BACKGROUND OF THE DISCLOSURE

The vestibular system of the inner ear enables a person to perceive body position in relation to the eye movements. The vestibular system helps in controlling the balance and eye movements of a person. In an effort to assess the integrity of the vestibular system, it is often useful to test its performance.

Vestibular examination involves the measurement of the Vestibulocular reflex (VOR). The function of the VOR is to keep the image of the object of interest on the retina during the head movement. The magnitude and direction of the eye movement depends on the signal provided by the vestibular system. Hence, the observations of eye movement also provide a basis for inferring the state of the vestibular system.

The VOR is the main driving force in the vestibular system which can stabilize images on the fovea during sudden and high speed head acceleration. Further, the VOR provides a reflex eye movement that stabilizes images on the retina during head movement of a person. Such image stabilization is performed by producing an eye movement in the direction opposite to head movement, at an amplitude and velocity that matches the head movement, thus preserving the image on the center of the visual field.

For example, when the head moves to the right, the eyes move to the left, and vice versa. During most of the time, every person has slight head movements. Accordingly, the VOR is very important for stabilizing vision of patients during movement. In all these cases, the patient cannot stabilize the eyes during small head movements. The VOR reflex does not depend on visual input and works even in total darkness or when the eyes are closed.

Many recent studies of patients with vestibular disorders have more specifically investigated the role of the vestibular system in controlling gaze, balance, posture, and sensory substitution. During movements, sensory information from somatosensory, vestibular and visual systems is integrated based on the goal of the action. The VOR, which functions to stabilize gaze and ensure clear vision during everyday activities, has been well characterized and shows impressive adaptation in response to behavioral requirements.

The VOR is a three neuron reflex arc with a latency of less than 10 msec. The relative simplicity of the pathways that mediate the VOR, have made it an excellent model system for bridging the gap between the cells, neuronal circuits, and behavior. The vestibular system also plays a critical role in ensuring postural equilibrium by producing appropriate adjustments during both self-generated movements and externally applied disturbances. These findings of clinical, behavioral and neurophysiological studies have led to a better understanding of the role of the vestibular system during every day activities.

Furthermore, balance disorders may be life-altering, as they can lead to falls, which account for up to 80 percent of all hospital admissions in older patients. Falls are a significant reason for fractures and loss of independence. Because of this, balance and vestibular disorders should be accurately diagnosed and treated promptly. Further, patients with vestibular deficits often complain of head movement-induced dizziness or head movement-induced blurring of vision i.e. oscillopsia. These problems are more severe in patients with bilateral vestibular hypofunction. Both of these problems are due to decrease in gain of VOR.

At present, the tests for identifying vestibular disorders and gaze acuity are manual. In manual testing the examiner has to manually note the degree of correctness of each graphic pattern or line present on the Snellen chart or on the LogMAR chart as read by the patient while rotating his head at constant speed. However, these manual recordings have some drawbacks and do not always provide the accurate test values. Further, the examiner does not have an accurate method of finding the speed of rotation of head.

Despite being very common, vestibular disorders are difficult to diagnose because of difficulty in selecting the right diagnostic criteria as well as the lack of accuracy in the test values. Further, it is not possible to accurately test the gaze instability during the left head rotation & the right head rotation at a constant speed. Therefore, there is need of a method and system for accurately diagnosing and treating vestibular disorders in more efficient manner. Further, there is a need for accurately determining the gaze stability of the person while head rotation at a constant speed.

SUMMARY OF THE DISCLOSURE

In view of the foregoing disadvantages inherent in the prior-art and the needs as mentioned above, the general purpose of the present disclosure is to provide a system and method for identifying the dynamic gaze stability in response to the rotational head movement of a patient, including all advantages of the prior art and to overcome the drawbacks inherent in the prior art and offering some added advantages.

To achieve the above objectives and to fulfill the identified needs, in one aspect, the present disclosure provides an apparatus for identifying the dynamic gaze stability in response to the rotational head movement of a patient. The apparatus includes a head mounted device configured to a patient head, wherein the head mounted device is adapted to track the movement of the patient head. Further, the apparatus includes a display adapted to recurringly display a plurality of graphic patterns, a perception module adapted to receive a plurality of perception information regarding the patient's call out of the said recurringly displayed graphic patterns and a data processing device adapted to control and execute function of the said display and the said head mounted device, wherein the said control is based on the inputs given by the perception module.

In another aspect, the present invention provides a method for identifying a gaze stability of the patient. The method includes a step measuring a static visual acuity value of the patient. The said static visual acuity value is measured by allowing the patient to read a graphic pattern while keeping the head in a static position. Further, the method includes a step of measuring a dynamic visual acuity value of the patient. The said dynamic visual acuity value is measured by allowing the patient to read a graphic pattern while moving the head at particular speed in a particular direction and angle. The said dynamic visual acuity value is determined close to hundred percent accuracy by using a head mounted device, a display, a perception module, and a data processing device.

Furthermore, the method includes a step of measuring the said static visual acuity value and the dynamic visual acuity value within the same physical test conditions. After measuring the said static visual acuity value and the dynamic visual acuity value, the method includes a step of comparing the said static visual acuity value with the said dynamic visual acuity value. Thereafter, the method includes a step of displaying the comparative value as a gaze stability value.

In another aspect, the present invention provides an apparatus and method for determining and diagnosing the visual acuity or the dynamic gaze stability in an automatic/manual manner.

In another aspect, the present invention provides an apparatus and method for identifying an accurate visual acuity of the patient under various head movement conditions. The head movement condition can be any one of rotation in a horizontal plane i.e. left to right, and/or right to left, or rotation in a vertical plane i.e. up to down, and/or down to up. While, rotating the head in a horizontal plane i.e. from left to right or right to left, the speed of rotation should be minimum 120 degree per second. During the test for side to side rotation, the head should be flexed 30 degrees down so that the lateral semi-circular canals are in a plane of test conditions required for measuring the dynamic visual acuity value.

In another aspect, the present invention provides an apparatus and method for providing assistance to the patient for maintaining the necessary condition while performing dynamic gaze stability test for more accurate results.

This together with the other aspects of the present invention along with various features of novelty that characterized the present disclosure is pointed out with particularity in claims annexed hereto and forms a part of the present invention. For better understanding of the present disclosure, its operating advantages, and the specified objective attained by its uses, reference should be made to the accompanying descriptive matter in which there are illustrated exemplary embodiments of the present invention.

BRIEF DESCRIPTION OF THE DRAWINGS

The advantages and features of the present disclosure will become better understood with reference to the following detailed description and claims taken in conjunction with the accompanying drawing, in which:

FIGS. 2A-2D illustrate embodiment 20 providing different type of graphic patterns used for identifying the static and dynamic visual acuity of a patient, according to various embodiments of the present invention;

Like numerals refer to like elements throughout the present disclosure.

DETAILED DESCRIPTION OF THE DISCLOSURE

The foregoing descriptions of specific embodiments of the present disclosure have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

The terms "a" and "an" herein do not denote a limitation of quantity, but rather denote the presence of at least one of the referenced item.

The terms "having", "comprising", "including", and variations thereof signify the presence of a component.

The term "visual acuity" herein refers to degree of sharpness of the vision, measured by the ability to discern letters or numbers at a given distance according to a fixed standard.

The term "perception information" herein refers to the reading data created by reading the graphic pattern displayed on the screen (voice data, or any written data).

The present invention provides an apparatus for identifying the dynamic gaze stability in response to the rotational head movement of a patient. The apparatus and its usage are described with reference to FIGS. 1-3, whereas the method for identifying the dynamic gaze stability using the present apparatus is shown with reference to FIG. 4. It should be apparent to a person skilled in the art that the term "apparatus" as referenced herein refers to a computerized setup that allows an individual to automatically identifying the dynamic gaze stability.

Figure 1:
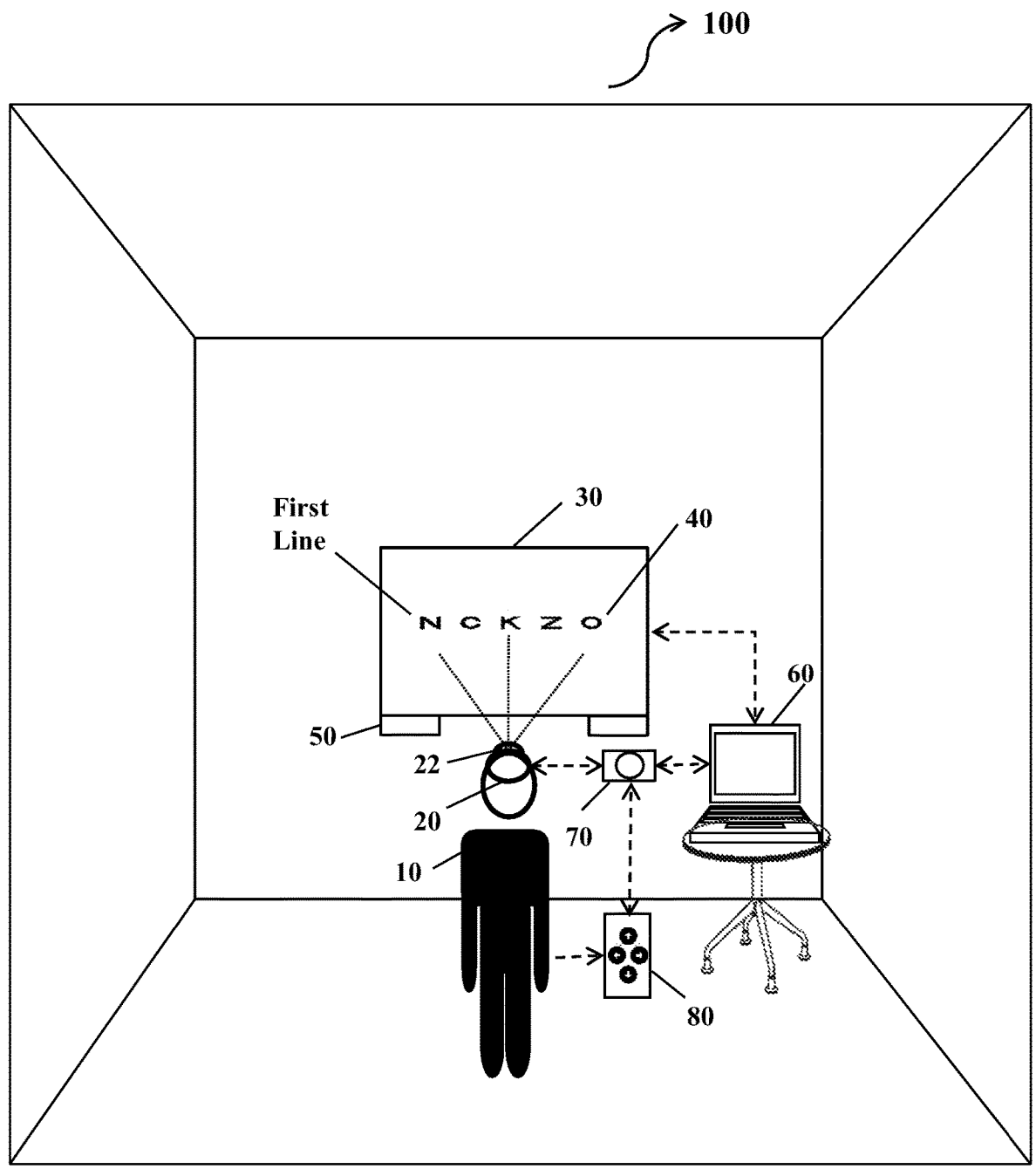
FIG. 1 illustrates embodiment 10 providing a schematic representation of an apparatus for identifying the dynamic visual acuity in response to the rotational head movement of a patient, according to various embodiments of the present invention.

As per embodiment 10 of the present invention, FIG. 1 illustrates the arrangement of various parts of the present apparatus used for identifying the dynamic visual acuity in response to the rotational head movement of a patient. As shown in FIG. 1, a patient 10 is made to sit at least two meter away from the display 30. Further, the apparatus 100 includes a head mounted device 20 configured to the head of the patient 10. The said head mounted device 20 is adapted to track the head movement of the patient. Further, the head mounted device 20 can be selected from at least one of a laser device, a gyro sensor, a camera, any movement tracking device adapted for tracking the movement of the head 10 of the patient.

Further, the apparatus 100 includes a display 30 adapted to recurringly display a plurality of graphic patterns 40 as shown in FIG. 1. The display 30 includes a plurality of sensors 50 adapted to track the laser light projection 22 (as shown in FIG. 1) as projected from the head mounted device 20. The said plurality of sensors is adapted for tacking the movement of the head 10 of the patient with respect to the display 30.

In an exemplary embodiment, the sensor 50 as used herein is a laser sensor. The laser sensor 50 is adapted to track the movement of the projection of laser light 22 from the head mounted device.

In another embodiment, the head mounted device 20 includes a Gyro sensor instead of the laser light projection 22 which is adapted to track the patient's head angle, position and speed while preforming the visual acuity test.

Further, as shown in FIG. 1, the apparatus 100 includes a perception module 70 adapted to receive a plurality of perception information. The said perception information is the patient's call out of the said plurality of graphic patterns 40 as recurringly displayed on the display 30. The said perception module 70 includes at least one of a microphone, a headphone, a transmitter, a receiver, a gesture/signage detection screen, a camera, an input device, sensors and a combination thereof. Further, the perception module 70 is adapted for transmitting the said received perception information to a data processing device 60. Further, the perception information is at least one of a voice data, a visual data, or a digital data of the patient's call out of the said plurality of graphic patterns 40 as recurringly displayed on the display 30.

The perception module 70 as provided herein can be either an automated platform or a manual platform. In an automated platform, the perception module automatically detects the voice of the patient via a voice recognition system. The said voice includes the patient's call out of the graphic patterns 40 as recurringly displayed on the display 30. In another exemplary embodiment, the perception module is adapted to detect the gesture, signage as provided by the patient. Accordingly, the perception module 70 is adapted for automatically receiving and transmitting the patient's call out of the said graphic patterns 40 to the data processing device 60.

In another embodiment, the said automated platform includes a remote device 80 having a plurality of buttons representing the direction of the alphabets as appearing on the graphic pattern 40. The said remote device 80 can be used in circumstances when the patient is unable to call out the graphic patterns 40 as displayed on the display 30 such as a mute patient. In this case, the graphic patterns 40 are presented having alphabets directed into different directions such an example of the graphic patter 40 is provided in FIG. 2D. The said graphic pattern 40 provides an optotype where the alphabet "E" is represented in different directions. When such a graphic pattern 40 is displayed to the patient than the patient click the buttons of the said remote device 80 in accordance to the direction of the alphabets as present in the graphic pattern 40. Accordingly, a sequence of clicking the buttons of the said remote device 80 is produced by the patient. The said sequence of clicking the buttons of the said remote device 80 is then transmitted to the said perception module 70. In this case the said sequence of clicking the buttons of the said remote device 80 is termed as the patient's call out or perception information of the said graphic patterns 40. Accordingly the said remote device 80 is also used by the patient for giving the perception information to the said perception module 70 and then to the said data processing device 60.

In a manual platform, the perception module includes human assistance such as a doctor or any other person. The human assistance receives the patient's call out of the said graphic patterns 40 and enters the same to the data processing device 60.

In one embodiment of the present invention, the data processing device 60 is adapted to validate the correctness of the received perception information. Further, the data processing device 60 identifies a degree of correctness of the said received perception information of the selected graphic patterns 40 as recurringly displayed on the display 30.

Further, based on a degree of correctness of said perception information, the data processing device 60 is adapted to change or adjust the graphic patterns 40 and display the said changed graphic patterns 40 to the patient 10.

Further, the degree of correctness of said perception information includes accuracy percentage of reading the said graphic pattern. Further, the data processing device 60 is adapted to determine the degree of correctness by matching the said perception information of the selected graphic patterns 40 with the pre-stored information of the selected graphic patterns 40 as present in the data processing device 60. Further, the data processing device 60 is adapted to identify and mark the graphic patterns 40 as the dynamic visual acuity value or static visual acuity value when the said degree of correctness is less than a pre-defined threshold value i.e. less than sixty percent (60%). Further, the said pre-defined threshold value is set by a doctor according to the test requirements while performing the visual acuity test on the patient. The said pre-defined threshold value is selected in the range from 20%-100%.

In a preferred embodiment, the said graphic patterns 40 as provided herein includes a Log Mar chart, where different alphabets are arranged in lines of variable size. The present system is preferably adapted to display one line of the said alphabets at one time. In this manner, the first line as shown in FIG. 1 is displayed at the starting of the test. If the perception information as provided by the patient is correct with respect to the first line then the data processing device displays the second line of the graphic pattern as provided in FIG. 2. If the perception information as provided by the patient is correct with respect to the second line then the data processing device displays the third line of the graphic pattern, and so on the data processing device continue to display the next line till the perception information falls below a pre-defined threshold value.

In another embodiment, the graphic patterns 40 include different alphabets, numerals, images and/or symbols arranged in several rows of optotypes. Every row depicts optotype of different size. Further, every time a new row is randomly generated and accordingly the patient cannot remember the previous row of the said graphic pattern 40.

This process of checking the correctness of the first line and then displaying the next line is repeated again and again by the data processing device 60. The process stops when the correctness of patient's call out of the graphic pattern 40 falls below sixty percent. Now, at this stage the data processing device 60 stops the displaying of the graphic pattern to the patient and the accurate test value is determined by the last line which the patient correctly perceived.

In another embodiment, the data processing device 60 is adapted to display one or more lines of the graphic pattern over the display 30 in a single step. In this process the patient is asked to identify one or more lines of the displayed graphic pattern 40. Further, in this process also the data processing device 60 stops the displaying of the graphic pattern to the patient when the correctness of patient's call out of the graphic pattern 40 falls below the pre-defined threshold value i.e. sixty percent. Now, at this stage the accurate test value is determined by the last line which the patient correctly perceived and where the correctness of patient's call out is equal to or below the pre-defined threshold value.

In one embodiment of the present invention, the data processing device 60 is adapted to control and execute the function of the display 30, the head mounted device 20, and the perception module 70. Further, the data processing device 60 is adapted to couple with the head mounted device 20, display 30 and perception module 70 for sending and receiving the information data via wired or wireless communication.

In one embodiment of the present invention, the data processing device 60 is a processor enabled device having a memory (not shown) for storing the said graphic pattern 40. The said data processing device 60 selects the said plurality of graphic patterns based on a plurality of predefined conditions and displays the selected graphic patterns over the display 30. Wherein, the predefined condition is at least a movement of the patient's head at a predefined speed in a particular direction and angle.

In one embodiment, the apparatus 100 is adapted to identify static visual acuity without head movement. In this process, the patient 10 is made to sit 2 meter away from the display 30 and keep the head in a static position. Further, the data processing device 60 is adapted to display the graphic patterns 40 over the said display 30 one at a time. In this situation, there is no need for any pre-defined condition (i.e. head movement) for displaying the graphic patterns 40. Thereafter, the patient 10 is asked to read the graphic patterns as displayed.

Further, such reading of the graphic patterns 40 in static position provides a reading data which herein referred to as "static perception information". The perception module 70 is adapted to receive the static perception information and transfer said information to the data processing device 60. Further, the data processing device 60 is adapted to validate the degree of correctness of the said static perception information e.g. the number/percentage of correctly read graphic patterns 40. Further, the data processing device 60 is adapted to automatically or manually decrease the size of the graphic patterns 40 or change the graphic patterns 40 based on the degree of correction. Further, data processing device 60 is adapted to mark the graphic pattern as the static visual acuity value when the said degree of correctness is less than sixty percent.

In one embodiment, the apparatus 100 is adapted to identify dynamic visual acuity head movement. In this process, the patient 10 is made to sit 2 meter away from the display 30. Further, the data processing device 60 is adapted to display the graphic patterns 40 over the said display 30 one at a time based on the predefined condition. In this situation, there is a need to meet the pre-defined condition (i.e. head is tilted 30 degree down from front and the rotation of head in a horizontal plane i.e. from left to right or right to left at minimum speed of 120 degree per second) for displaying the graphic patterns 40. Thereafter, the patient 10 is asked to read the graphic patterns. Further, such reading of the graphic patterns 40 in dynamic position provides a reading data which herein refer as "dynamic perception information".

Further, the data processing device 60 is adapted to receive the said dynamic perception information of the graphic pattern from the patient via the perception module 70 as stored in the memory (not show) of the data processing device 60. Further, the data processing device 60 is adapted to validate the degree of correctness of the said dynamic perception information. Further, the data processing device 60 is adapted to identify and mark the graphic patterns 40 as the dynamic visual acuity value when the said degree of correctness is less than sixty percent.

Further, the data processing device 60 is adapted to retrieve the static visual acuity value and the dynamic visual acuity value from the memory (not shown). Further, the data processing device 60 is adapted to determine a comparative value based on the static visual acuity value and the dynamic visual acuity value. Further, the data processing device 60 is adapted to display the comparative value as a gaze stability value to the patient 10.

It should be noted that any features of the embodiment 10 may be readily combined or permuted with any of the embodiments 20, 30, and/or 40 in accordance with the invention.

As per embodiment 20 of the present invention, FIG. 2 illustrates the graphic patterns 40 which is at least one of a plurality of letters, Optotype (alphabets), symbols, a plurality of numbers, and a plurality of digital images, a Log Mar eye chart, or a combination thereof. Further, the data processing device 60 is adapted to change and/or adjust the size, the font, the color, and pixel of the selected graphic patterns as appearing on the screen of the display 30 as shown in 2C. Further, the data processing device 60 is adapted to insert additional letter to the said graphic patterns 40. Accordingly, every time a new row of the said graphic pattern 40 is randomly generated and accordingly the patient cannot remember the previous row of the said graphic pattern 40.

In one embodiment of the present invention, the data processing device 60 can be selected from at least one of a computer, a smartphone, or any processor enabled device.

It should be noted that any features of the embodiment 20 may be readily combined or permuted with any of the embodiments 10, 30, and/or 40 in accordance with the invention.

Figure 3:
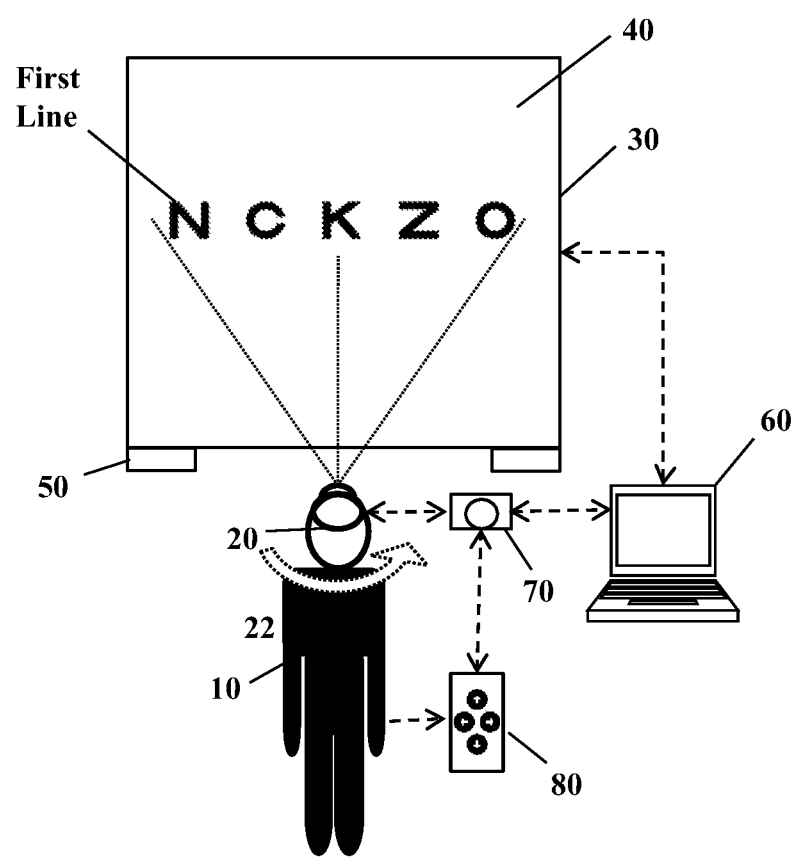
FIGS. 3-3B illustrate embodiment 30 providing head rotation and head movement as performed while using the apparatus for identifying the dynamic visual acuity, according to various embodiments of the present invention.
Figure 3A:
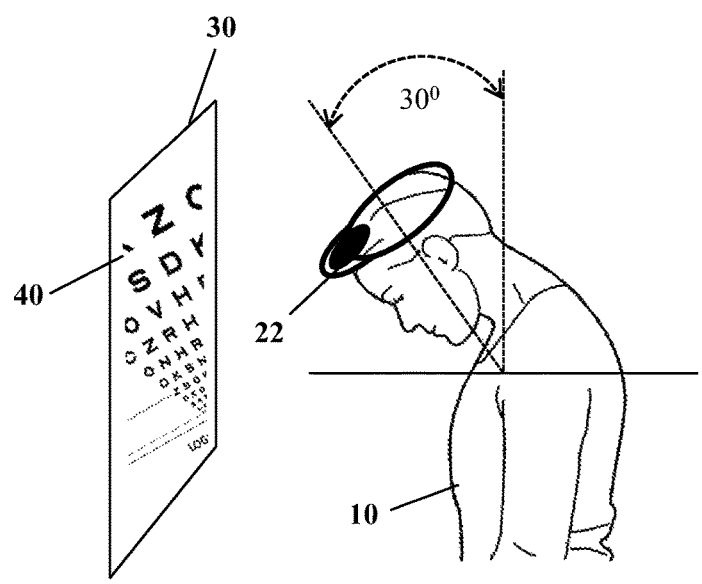
Figure 3B:
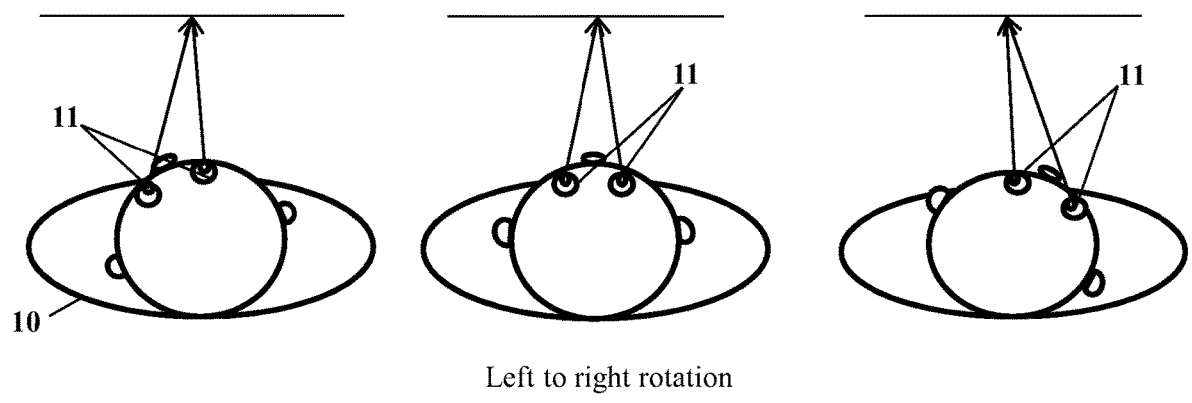

As per embodiment 30 of the present invention, FIG. 3 illustrates rotation and movement of the patient's head as performed while using the apparatus 100 for identifying the dynamic visual acuity.

The apparatus 100 includes a head mounted device 20 having a laser light projection 22. The said head mounted device 20 is adapted to be placed over the head of the patient 10. Further, the laser sensor 50 is place on the said display 30. The said laser sensor 50 is adapted to send the patient head movement information (including rotation direction and speed of the rotation) to the data processing device 60.

In a preferred embodiment, the patient is allowed to tilt the head in forward direction at 30 degree angle so that the lateral semi-circular canals of the patient are in the plane of testing. The Gyroscope as provided in the head mounted device accurately measures the 30 degree angle tilt of the patient' head. Thereafter, the patient is allowed to rotate the head in a horizontal plane i.e. from left to right at a speed equal to or more than 120 degree per second and less than 180 degree per second.

Further, it is important to keep the head tilted at 30 degree forward while rotating the head form left to right or right to left direction. The laser light 20 projection as present on the head mounted device and the laser sensor 50 measures the left to right head movement at the prescribed seed. The tilting and the left to right rotation at the prescribed head position, angle and speed is considered as the predefined condition. Further, the patient 10 is asked to read the graphic patterns 40 while moving the head from left to right or right to left direction to meet the predefine condition for displaying the graphic pattern on the display 30.

Further, the data processing device 60 is adapted to display the graphic patterns 40 (letters) one at a time based on the pre-defined condition. If the rotation direction and speed of the rotation of the patient's 10 head does not meet the pre-defined condition, the data processing device 60 does not display the graphic patterns 40.

Further, if the rotation direction and speed of the rotation of the head of the patient meets the pre-defined condition, then the data processing device 60 is adapted to display the graphic patterns 40 (Optotypes (alphabets) according to the LogMAR chart) on the display 30. Further, the data processing device 60 is adapted to identify the degree of correctness for e.g. the number of correctly read graphic patterns 40 from the perception information by patient 10. Further, the data processing device 60 is adapted to determine a dynamic visual acuity value based on the degree of correctness of the last perception information received from the perception module 70.

In a preferred embodiment, the graphic patterns 40 as provided herein includes a Log Mar chart, where different letters are arranged in different lines of variable size and fonts. The present system is preferably adapted to display one line of letters at one time. In this manner, the first line as shown in FIG. 1 is displayed at the starting of the test. The patient is asked to read the said graphic pattern while rotation his/her head form left to right, right to left. If the perception information as provided by the patient is correct with respect to the first line then the data processing device display second line of the graphic pattern as provided in FIG. 2. If the perception information as provided by the patient is correct with respect to the second line then the data processing device display third line of the graphic pattern.

This process of checking the correctness of the first line and then displaying the next line is repeated again and again by the data processing device 60. The process stops when the correctness of patient's call out of the said graphic patterns 40 falls below sixty percent. Now, at this stage the data processing device 60 stops the displaying of the graphic pattern to the patient and the accurate test value is determined by the last line which the patient correctly perceived.

In one embodiment of the present invention, the apparatus 20 may use a gyro sensor 22 for measuring the angle of patient head which should tilted 30 degree from front. Further, the gyro sensor 22 (may be coupled to the head mounted device 20. Further, the gyro sensor 22 is adapted to send the head movement data to the data processing device 60.

In yet another embodiment, the data processing deceive 60 is adapted to provide an audio output (not shown) as a clue for maintaining the speed or rotation of the patient's head at desired level to meet the pre-defined condition to a patient 10.

In yet another embodiment, the display 30, the head mounted device 20, the perception module 70 and the data processing device 60 are interconnected for sending and receiving information data via wired or wireless communication.

In yet another embodiment, the data processing device 60 is operated by a doctor (not shown). Further, the doctor (not shown) is adapted to work as a perception module 70. Here, the patient speaks out the Optotype alphabets or graphic patterns 40 (perception information) that are displayed to the patient. Further, the doctor is adapted to watch or hear and record the patient's call out of the said graphic pattern and operate the data processing device 60 accordingly. Further, the doctor gives an input to the data processing device 60 to decrease the size of the next graphic patterns 40 (Optotype alphabets). Further, the doctor is adapted to select the said graphic patterns 40 via data processing device 60 and send the same to the displaying module 30 for displaying to the patient.

It should be noted that any features of the embodiment 30 may be readily combined or permuted with any of the embodiments 10, 20, and/or 40 in accordance with the invention.

Figure 4:
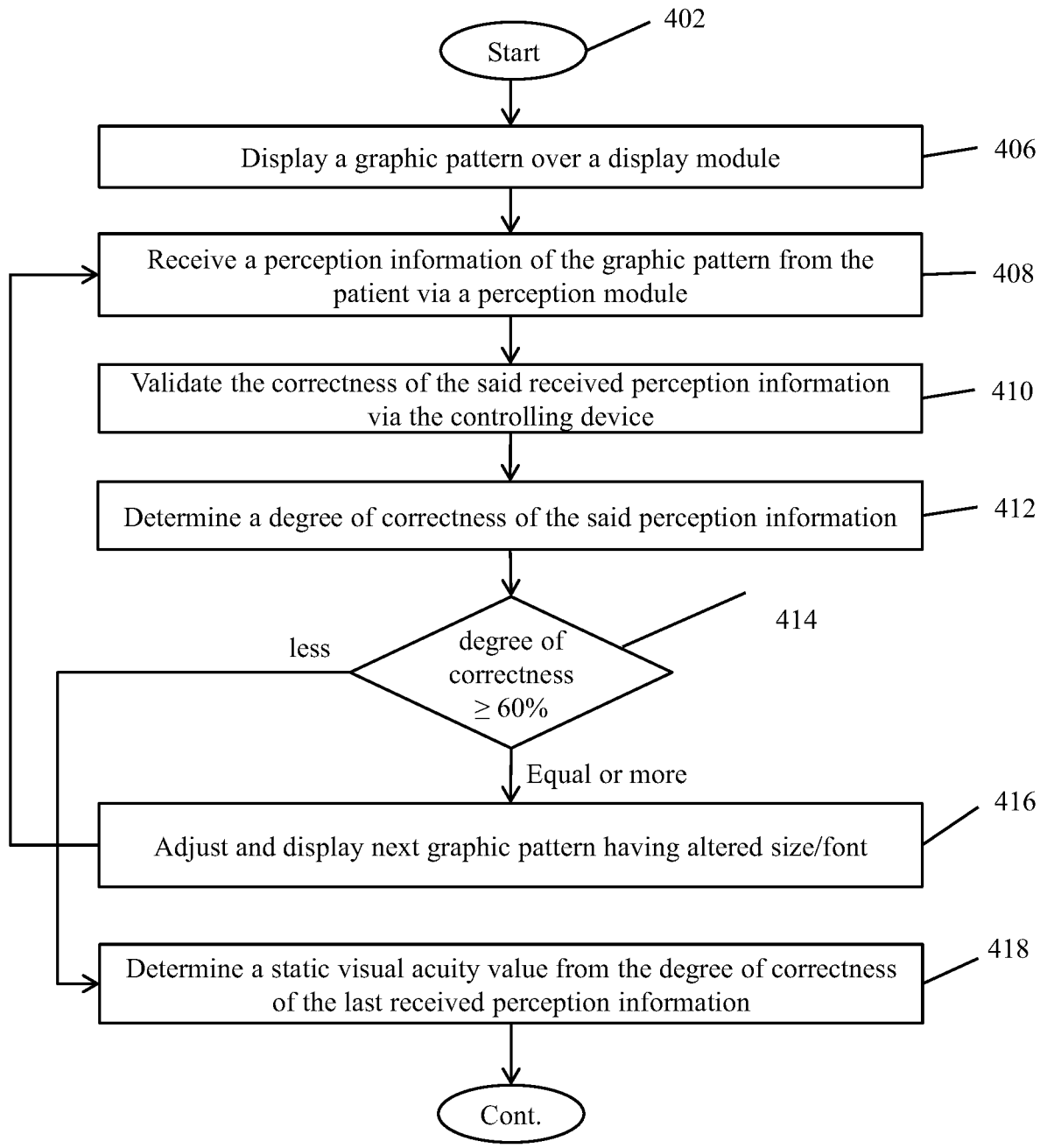
FIGS. 4-4A illustrate embodiment 40 providing flow charts to identify the gaze stability value by the present apparatus and method, according to various embodiments of the present invention.
Figure 4A:
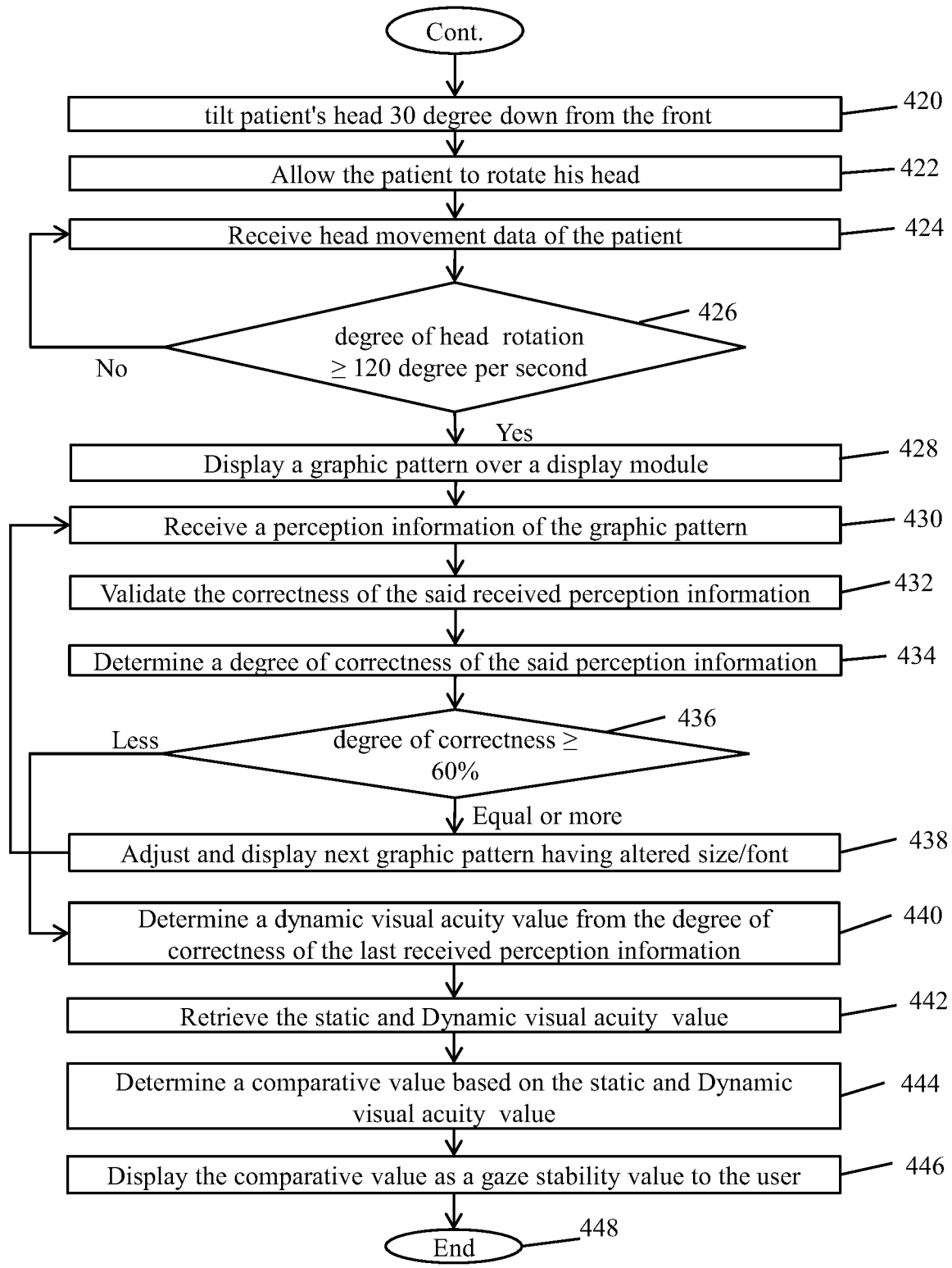

As per embodiment 40 of the present invention, FIGS. 4-4A illustrates a method for determining the gaze stability value via the apparatus 100 according to various embodiment of the present invention. The method starts a static visual acuity test at step 402. Further at step 406, the method is adapted to display graphic patterns 40 over a display 30. Further, the method is adapted to receive perception information of the graphic patterns 40 from the patient 10 via a perception module 70 at step 408. Further, the method is adapted to validate the correctness of the said received perception information via the data processing device 60 at step 410.

Thereafter, the method is adapted to determine a degree of correctness of the said perception information at step 412. Further at step 414, the method is adapted to check the degree of correctness. Further, if the degree of correctness is more than 60%, the method is adapted to adjust and display next graphic patterns 40 having altered size/font at step 416. Further, the method is adapted to repeat the process from steps 408 to 414 till the degree of correctness become less than 60%.

In case, the degree of correctness is less than 60% at step 414, the method is adapted to determine a static visual acuity value from the degree of correctness of the last received perception information at step 418. Further, the method is adapted to move to towards dynamic visual acuity test.

Now again referring to FIGS. 4-4A, the dynamic visual acuity test starts from step 420. Further, the method allows a patient 10 to tilt his head at 30 degree down from front at step 420. Further, the method allows the patient to rotate his head from left to right more than 120 degree per second but not more than 180 degree per second.

Furthermore, the method is adapted to receive head movement data of the patient 10 via a head mounted device 20 at step 424. Thereafter at step 426, the method is adapted to check speed of head rotation. If the speed of the head rotation is less than 120 degree per second, then the method is adapted to repeat again the step 424 to 426 till the speed of the head rotation is equal to or more than 120 degree per second.

Now if the speed of the head rotation is equal to or more than 120 degree per second at step 426, than the method is adapted to recurringly display a plurality of graphic patterns 40 over a display 30 at step 428.

Further at step 430, the method is adapted to receive perception information of the graphic pattern 40 from the patient via a perception module 70. Further, the method is adapted to validate the correctness of the said received perception information via the data processing device 60 at step 432. In one embodiment, the patient speaks out the letters (perception information) that are displayed and the doctor gives an input to the data processing module to decrease the size of the optotype.

Further at step 434, the method is adapted to determine a degree of correctness of the said perception information. Further at step 436, the method is adapted to check the degree of correctness. Again at step 436, if the degree of correctness is more than 60%, than the method is adapted to adjust and display next graphic pattern 40 having altered size/font at step 438 and repeat the steps 430 to 436 till the degree of correctness become less than 60%.

In case the degree of correctness is less than 60% at step 436, the method is adapted to determine a static visual acuity value from the degree of correctness of the last received perception information at step 440.

It should be noted that any features of the embodiment 40 may be readily combined or permuted with any of the embodiments 10, 20, and/or 30 in accordance with the invention.

After step 440, the method is adapted to retrieve the static visual acuity value & the Dynamic visual acuity value at step 442. Further, the method is adapted to determine a comparative value based on the static visual acuity value & the dynamic visual acuity value at step 444. Further, the method is adapted to display the comparative value as a gaze stability value to the patient 10. Further, the method stops at 446.

Figure 5A:
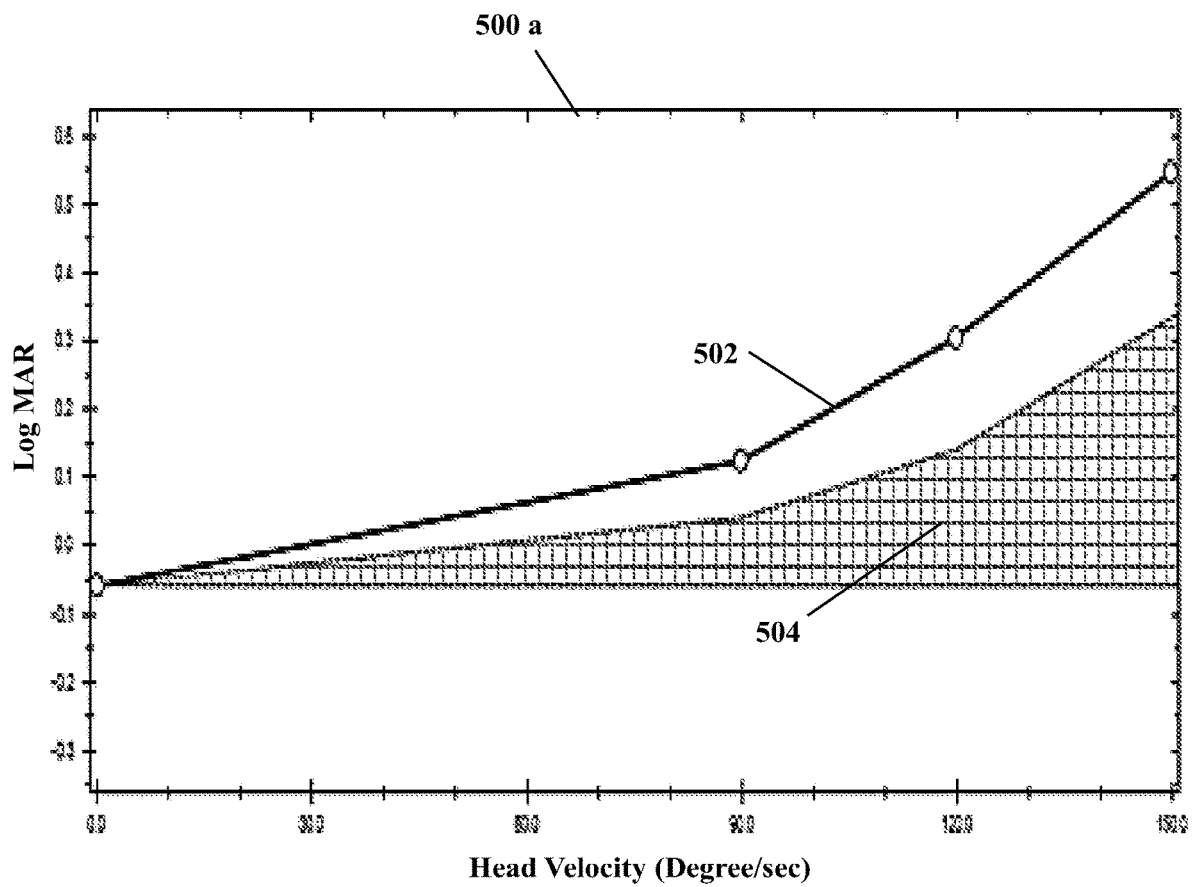
FIGS. 5A-5B illustrate an exemplary embodiment 50 providing abnormal and normal dynamic visual acuity graph based on the head movement data of the patient, according to various embodiments of the present invention.
Figure 5B:
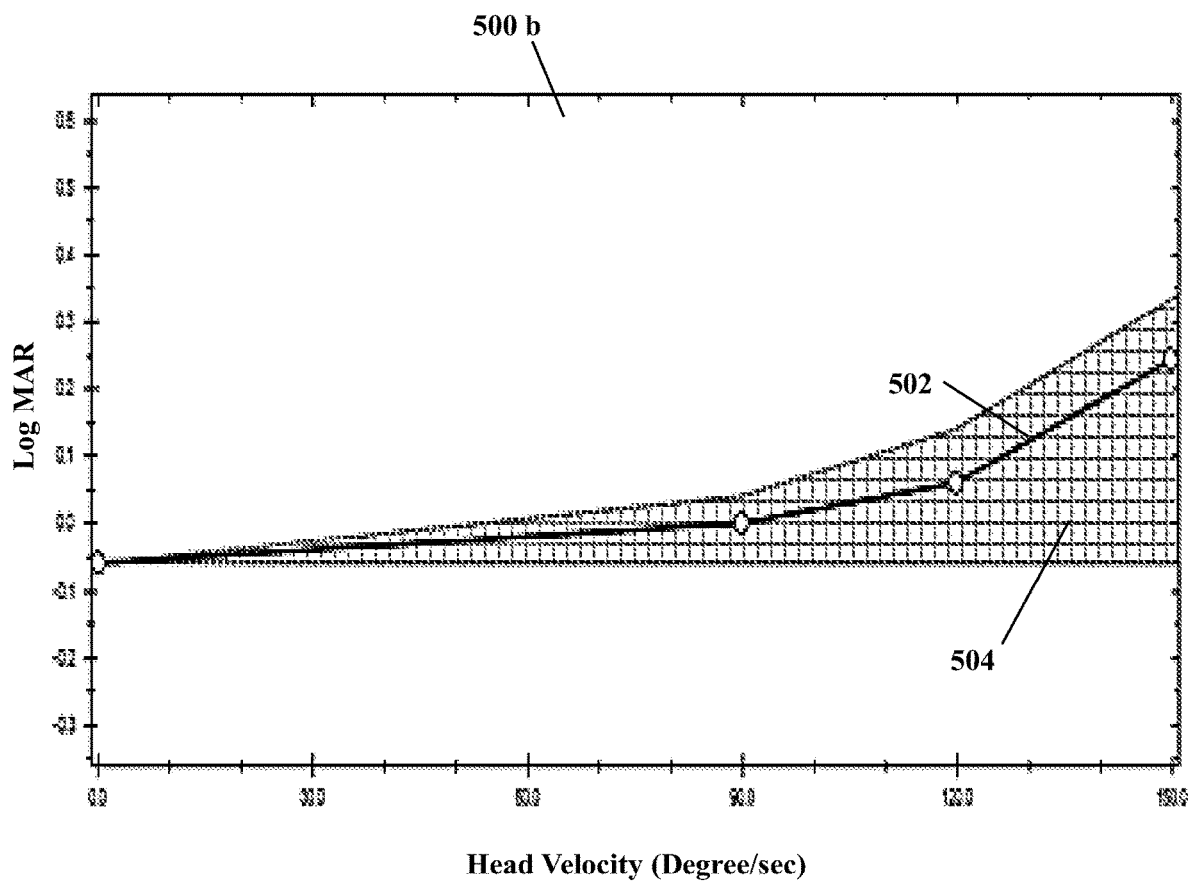

As per embodiment 50 of the present invention, FIG. 5A illustrate abnormal dynamic visual acuity graph 500*a* and FIG. 5B illustrate normal dynamic visual acuity graph 500*b*. Further, both the graphs 500*a* and 500*b* includes a shaded area 504 which represent the normal dynamic visual acuity of a person. Further, the graphs 500*a* and 500*b* includes a line 502 which represent the perception information data of the patient while performing the dynamic visual acuity test. Further, in one embodiment, the data processing device 60 is adapted to generate the said graphs 500*a* and 500*b*. These graphs are based on the perception information as received from the patient while moving the head.

In FIG. 5A, the line 502 which represent the perception information data of the patient while rotating the head. It is to be noted that the line 502 is beyond the shaded area 504 and hence the said patient has abnormal visual acuity. Similarly, FIG. 5B illustrates the normal dynamic visual acuity as the perception information line 500 is under the shaded area 504.

It should be noted that any features of the embodiment 50 may be readily combined or permuted with any of the embodiments 10, 20, 30 and/or 40 in accordance with the invention.

Further, the method is adapted to determine a gaze stability value based on the comparison of degree of correctness of the perception information during the static and dynamic visual acuity tests. The said present method is adapted to be carried out at various speeds and directions of the patient's head as per various embodiments of the present invention.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

We claim:

1. An apparatus for identifying a gaze stability of the patient by measuring and comparing a static visual acuity value and a dynamic visual acuity value of the patient, the apparatus comprising:

a head mounted device configured to a head of a patient, wherein the head mounted device is adapted to track movement of the patient's head in horizontal and vertical plane;

a display capable of displaying graphic patterns to the patient;

an automated perception module adapted for receiving a perception information from the patient automatically through a recognition system, wherein the said perception information is the patient's call out of the said displayed graphic patterns; and a data processing device coupled to the perception module and adapted to recurringly change the graphical patterns on the said display, wherein the said recurring display of the graphical patterns is based on a correctness value of the perception information and on a plurality of predefined conditions, wherein the data processing device is further adapted to calculate the gaze stability by comparing the correctness value of the perception information in a static and dynamic test condition, and wherein the said plurality of predefined conditions comprises tilting the head of the patient forward at about 30 degrees and rotating the head in a horizontal plane, such that the predefined conditions are satisfied when the said head rotation in the horizontal plane is equal to or more than 120 degrees per second and less than 180 degrees per second.

2. The apparatus as claimed in claim 1, wherein the head mounted device is selected from at least one of a laser light indicator, a gyro sensor, or a motion tracking device.

3. The apparatus as claimed in claim 1, wherein the display is at least one of a digital screen having one or more laser sensors configured thereon.

4. The apparatus as claimed in claim 1, wherein the graphic pattern is selected from at least one of a plurality of letters, a plurality of Optotype alphabets, a plurality of numbers, a plurality of symbol, a plurality of images, and a Log Mar eye chart.

5. The apparatus as claimed in claim 1, wherein the perception module comprises at least one of a microphone, a headphone, a remote device, a transmitter, a receiver, and a camera.

6. The apparatus as claimed in claim 1, wherein the perception module is adapted for transmitting the said received perception information to the data processing device.

7. The apparatus as claimed in claim 6, wherein the perception information is at least one of a voice data, a visual data, or a digital data of the patient's call out of the displayed graphic pattern.

8. The apparatus as claimed in claim 1, wherein the data processing device comprises a processor enabled device having a memory for storing the said graphic patterns.

9. The apparatus as claimed in claim 8, wherein the data processing device is adapted to validate a degree of correctness of the received perception information, and based on the degree of correctness of said perception information, the data processing device adjusts and displays the recurring graphic patterns to the patient.

10. The apparatus as claimed in claim 9, wherein the data processing device is adapted to determine a visual acuity value in dynamic test condition of the patient when the said degree of correctness is equal to or less than a pre-defined threshold value.

11. The apparatus as claimed in claim 10, wherein the said pre-defined threshold value can be within range of twenty percent to hundred percent degree of correctness of the said perception information.

12. The apparatus as claimed in claim 8, wherein the data processing device is adapted to determine a visual acuity value in the static test condition of the patient when the said predefined condition is the static position of the head of the patient.

13. The apparatus as claimed in claim 1, wherein the display, the head mounted device, the perception module and the data processing device are interconnected for sending and receiving information data via wired or wireless communication.

14. A method for identifying a gaze stability of the patient, the method comprising steps of:
measuring a static visual acuity value of the patient through reading a plurality of graphic patterns recurringly displayed while keeping the head in a static position;
measuring a dynamic visual acuity value of the patient through reading a plurality of graphic patterns recurringly displayed while moving the head in a particular direction and angle at a predefined speed,
wherein the plurality of graphic patterns is recurringly displayed on the said display based on a correctness value of perception information of the graphical pattern displayed and on a plurality of defined conditions, and
wherein the said dynamic visual acuity value is determined via a head mounted device, a display, a perception module, and a data processing device, the said static visual acuity value and the dynamic visual acuity value are measured within the same physical test conditions;
comparing the said static visual acuity value with the said dynamic visual acuity value; and
displaying the comparative value as a gaze stability value, and
wherein the said plurality of predefined conditions comprises tilting the head of the patient forward at about 30 degrees and rotating the head in a horizontal plane, and wherein the predefined conditions are satisfied when the said head rotation in the horizontal plane is equal to or more than 120 degrees per second and less than 180 degrees per second.

15. The method as claimed in claim 14, wherein the said static visual acuity value of the patient is measured by the steps of:
allowing the patient to read a plurality of graphic patterns recurringly displayed while keeping the head in a static position;
receiving a static perception information of the said graphic patterns from the patient via a perception module;
validating degree of correctness of the said static perception information via a data processing device; and
marking the graphic pattern from the said plurality of graphic patterns as the static visual acuity value when the said degree of correctness is less than sixty percent.

16. The method as claimed in claim 14, wherein the said dynamic visual acuity value of the patient is measured by the step of:
allowing the patient to tilt the head forward at 30 degree and rotating the head in a horizontal plane at a speed equal to or more than 120 degree per second, and receiving a head movement data of the patient via the head mounted device;
displaying a plurality of graphic patterns recurringly over the display, wherein the said displaying of the plurality of graphic patterns is based on the said received head movement data;
allowing the patient to read the said recurringly displayed plurality of graphic patterns while rotating the head in a horizontal plane;
receiving a dynamic perception information of the said recurringly displayed plurality of graphic patterns from the patient via the perception module; validating the degree of correctness of the said dynamic perception information via a data processing device; and
marking the graphic pattern from the said recurringly displayed plurality of graphic patterns as the dynamic visual acuity value when the said degree of correctness is less than sixty percent.

17. The method as claimed in claim 16, wherein the head mounted device is adapted to track the head movement of the patient, the said device is selected from at least one of a laser, a gyro sensors, or a motion tracking device.

18. The method as claimed in claim 16, wherein the display is at least a digital screen, or a digital screen installed with one or more laser sensors working in conjugation with the said laser light indicator of the head mounted device.

19. The method as claimed in claim 16, wherein the said recurringly displayed plurality of graphic patterns are randomly generated and displayed, wherein the said graphic patterns is selected from at least one of a plurality of letters, a plurality of numbers, a plurality of digital images, a Log Mar eye chart, or a combination thereof.

20. The method as claimed in claim 16, wherein the perception information is at least a voice data, a visual data, a remote device key sequence pattern data, and a digital data of the patient's call out of the said recurringly displayed plurality of graphic patterns.

21. The method as claimed in claim 20, wherein the said remote device key sequence pattern data is a sequence of keys of the remote device as pressed by the patient.

22. The method as claimed in claim 16, wherein the data processing device is a processor enabled device having a memory for storing the said plurality of graphic patterns, the said data processing device selects the said plurality of graphic patterns based on a plurality of predefined conditions and displays the selected graphic pattern over the display.

23. The method as claimed in claim 16, wherein the data processing device is adapted to validate the correctness of the received dynamic perception information, and based on a degree of correctness of said information the data processing device adjusts and recurringly displays another graphic pattern to the patient.

24. The method as claimed in claim 23, wherein adjusting and recurringly displaying of another graphic pattern comprises a change in size, font, pixel, letters, and alphabets of the graphic patterns on the screen of the display.

25. The method as claimed in claim 23, wherein the adjusting and displaying of another graphic pattern to the patient is stopped when the degree of correctness is equal to or less than a pre-defined threshold value.

26. The apparatus as claimed in claim 25, wherein the said pre-defined threshold value can be within range of twenty percent to hundred percent degree of correctness of the said perception information.

* * * * *